(12) United States Patent
Brayden et al.

(10) Patent No.: US 6,423,334 B1
(45) Date of Patent: Jul. 23, 2002

(54) COMPOSITION AND METHOD FOR ENHANCING TRANSPORT ACROSS GASTROINTESTINAL TRACT CELL LAYERS

(75) Inventors: David J. Brayden; Jacqueline M. Dee, both of Dublin (IE)

(73) Assignee: Elan Corporation, plc, Dublin (IE)

( * ) Notice: Subject to any disclaimer, the term of this patent is extended or adjusted under 35 U.S.C. 154(b) by 0 days.

(21) Appl. No.: 09/163,510

(22) Filed: Sep. 30, 1998

Related U.S. Application Data (60) Provisional application No. 60/060,618, filed on Oct. 1, 1997.

(51) Int. Cl.[7] .............................. A61K 9/00; A61K 9/14; A61K 9/20; A61K 9/48
(52) U.S. Cl. .................... 424/439; 424/451; 424/464; 424/489; 424/400; 514/800; 514/802; 514/807; 514/808; 514/783; 514/784; 514/822
(58) Field of Search ................ 424/489, 450, 424/464, 465, 451, 455, 452, 456, 439, 400

(56) References Cited

U.S. PATENT DOCUMENTS

| | | | |
|---|---|---|---|
| 4,656,161 A | 4/1987 | Herr ........................... | 514/56 |
| 4,810,726 A | 3/1989 | Bistrian et al. ............. | 514/552 |
| 5,140,021 A | * 8/1992 | Maxson et al. .............. | 514/177 |
| 5,160,743 A | * 11/1992 | Edgren et al. ............... | 424/473 |
| 5,229,130 A | * 7/1993 | Sharma et al. .............. | 424/449 |
| 5,455,280 A | * 10/1995 | Baranowitz ................ | 514/763 |
| 5,660,865 A | * 8/1997 | Pedersen et al. ............. | 426/99 |
| 5,795,896 A | * 8/1998 | Lofroth et al. .............. | 514/256 |
| 5,853,755 A | * 12/1998 | Foldvari .................... | 424/450 |
| 6,069,165 A | 5/2000 | Andrieu et al. ............. | 514/428 |

FOREIGN PATENT DOCUMENTS

| | | |
|---|---|---|
| EP | 0 535827 A1 | 9/1992 |
| EP | 0 589843 A1 | 9/1993 |
| FR | WO 98/11881 A1 | 3/1998 |
| GB | WO 97/05903 A2 | 2/1997 |
| JP | 56122310 A * | 9/1981 |

OTHER PUBLICATIONS

Tomita, et al; Pharmaceutical Research, vol. 5, No. 6, "Enhancement of Colonic Drug Absorption by the Paracellular Permeation Route"; 1988; pp. 341–346.

Anderberg, et al; Pharmaceutical Research, vol. 10, No. 6, "Sodium Caprate Elicits Dilatations in Human Intestinal Tight Junctions and Enhances Drug Absorption by the Paracellular Route"; 1993; pp. 857–864.

Yeh, et al; Pharmaceutical Research, vol. 11, No. 8, "Effect of Medium–Chain Glycerides on Physiological Properties of Rabbit Intestinal Epithelium in Vitro"; 1994; pp. 1148–1154.

Irish Search Report Irish Patent Application No. 980809 Oct. 1, 1998.

* cited by examiner

Primary Examiner—James M. Spear
(74) Attorney, Agent, or Firm—Caesar, Rivise, Bernstein, Cohen & Pokotilow, Ltd.

(57) ABSTRACT

A composition for enteral administration having a non-ionic vegetable oil GIT absorption enhancer capable of increasing the enteral absorbability of drugs, especially oral absorbability of hydrophilic and macromolecular drugs. The non-ionic vegetable oil GIT absorption enhancer, particularly Babassu oil or a derivative thereof, is capable of enhancing the uptake of a drug from the gastrointestinal tract so as to allow therapeutically effective amounts of the drug to be transported across the GIT of an animal such as a human without significant toxic side effects.

15 Claims, 7 Drawing Sheets

COMPOSITION AND METHOD FOR ENHANCING TRANSPORT ACROSS GASTROINTESTINAL TRACT CELL LAYERS

This application claims the benefit of Provisional Application No. 60/060,618 filed Oct. 01, 1997.

FIELD OF THE INVENTION

The present invention relates to a composition and method for enhancing transport across gastrointestinal tract (GIT) cell layers in an animal. More particularly, the present invention provides an enteral composition which enhances the uptake of a drug across the GIT comprising a non-ionic vegetable oil GIT absorption enhancer, most particularly Babassu oil or a derivative of Babassu oil.

BACKGROUND OF THE INVENTION

While the vast majority of drugs are intended for systemic action, most drug formulations are designed for enteral or peroral administration primarily for ease of administration and patient compliance. However, the systemic availability of hydrophilic and or macromolecular drugs, particularly peptides, administered enterally or perorally is often too low to have any therapeutic affect. Limiting factors which can decrease overall peroral bioavailability of a drug include low solubility or chemical instability in the GIT, high gastrointestinal and or hepatic metabolism and poor intestinal membrane permeability. Low peroral bioavailability of a drug is typically undesirable and can lead to significant intra- and inter patient variability in drug bioavailability and therefore therapeutic performance.

The mammalian small intestine is composed of "finger-like" villi and crypts that are covered by a continuous layer of polarized, columnar epithelial cells. This epithelium, consisting of a heterogeneous group of cells, forms the interface between the external environment (the intestinal lumen) and the interstitial space. The most common epithelial cell is the enterocyte or the absorptive cell. This cell type is responsible for the majority of the absorption of both nutrients and drugs which occurs in the small intestine. It is highly polarized with distinct apical and basolateral membranes which are separated by tight junctions. The actin-rich tight junctions in conjunction with looser desmosomes maintain the continuity of the epithelium. Efficient regulation of the opening and closure of the tight junctions is a key event in the control of macromolecular movement across the epithelium.

Enterocytes have active transport mechanisms that drive the absorption of nutrients, electrolytes and water (occurs predominantly over the surface of the villus) and the secretion of electrolytes and water (occurs mainly in the crypts). The apical membrane has uniform microvilli measuring approximately 1 $\mu$m in height in which disaccharides and peptidases reside. This membrane also expresses receptor mediated transport systems (e.g., cobalamin) together with ion, monosaccharide, amino acid, peptide and fatty acid transporters. The basolateral membrane, in contrast, has smooth contours with no sugar and peptide hydrolayses. The $Na^+/K^+$ ATPase pump is localized in the basolateral membrane and permits the vectorial movement of ions and solutes.

The epithelial cells lining the lumenal side of the GIT are a major barrier to drug delivery following oral administration. However, there are four recognized transport pathways which can be exploited to facilitate drug delivery and transport: the transcellular, paracellular, carrier-mediated and transcytotic transport pathways. The ability of a drug, such as a conventional drug, a peptide, a protein, a macromolecule or a nano or microparticulate system, to "interact" with one or more of these transport pathways may result in increased delivery of that drug from the GIT to the underlying circulation.

Certain drugs utilize transport systems for nutrients which are located in the apical cell membranes (carrier mediated route). Macromolecules may also be transported across the cells in endocytosed vesicles (transcytosis route). However, many drugs are transported across the intestinal epithelium by passive diffusion either through cells (transcellular route) or between cells (paracellular). Most orally administered drugs are absorbed by passive transport. Drugs which are lipophilic permeate the epithelium by the transcellular route whereas drugs that are hydrophilic are restricted to the paracellular route.

Paracellular pathways occupy less than 0.1% of the total surface area of the intestinal epithelium. Further, tight junctions, which form a continuous belt around the apical part of the cells, restrict permeation between the cells by creating a seal between adjacent cells. Thus, oral absorption of hydrophilic drugs such as peptides. can be severely restricted. Other barriers to absorption of drugs may include hydrolyzing enzymes in the lumen brush border or in the intestinal epithelial cells, the existence of the aqueous boundary layer on the surface of the epithelial membrane which may provide an additional diffusion barrier, the mucus layer associated with the aqueous boundary layer and the acid microclimate which creates a proton gradient across the apical membrane. Therefore, new strategies for delivering drugs across the GIT cell layers are needed, particularly for hydrophilic drugs including peptides and proteins, and macromolecular drugs.

Numerous potential absorption enhancers have been identified. For instance, medium chain glycerides have demonstrated the ability to enhance the absorption of hydrophilic drugs across the intestinal mucosa (*Pharm. Res.* Vol 11:1148–54 (1994)). However, the importance of chain length and/or composition is unclear and therefore their mechanism of action remains largely unknown. Sodium caprate has been reported to enhance intestinal and colonic drug absorption by the paracellular route (*Pharm. Res.* 10:857–864 (1993); *Pharm. Res.* 5:341–346 (1988)). U.S. Pat. No. 4,545,161 discloses a process for increasing the enteral absorbability of heparin and heparinoids by adding non-ionic surfactants such as those that can be prepared by reacting ethylene oxide with a fatty acid, a fatty alcohol, an alkylphenol or a sorbitan or glycerol fatty acid ester. U.S. Pat. No. 5,229,130 discloses a composition which increases the permeability of skin to a transdermally administered pharmacologically active agent formulated with one or more vegetable oils as skin permeation enhancers.

Often, however, the enhancement of, drug absorption correlates with damage to the intestinal wall. Consequently, limitations to the widespread use of GIT enhancers is frequently determined by their potential toxicities and side effects. Additionally and especially with respect to peptide, protein or macromolecular drugs, the "interaction" of the GIT enhancer with one of the transport pathways should be transient or reversible, such as a transient interaction with or opening of tight junctions so as to enhance transport via the paracellular route.

SUMMARY OF THE INVENTION

The present invention satisfies the above needs by providing a composition having a non-ionic vegetable oil GIT absorption enhancer for increasing the enteral absorbability of drugs, especially oral absorbability of hydrophilic and macromolecular drugs. The non-ionic vegetable oil GIT absorption enhancer is capable of enhancing the uptake of a drug from the gastrointestinal tract so as to allow therapeutically effective amounts of the drug to be transported across the GIT of an animal such as a human without significant toxic side effects.

The non-ionic vegetable oil GIT absorption enhancer of this invention is capable of transiently interacting with at least one transport pathway, preferably the paracellular or transcellular pathway so as to increase the transport of a drug between or through cells in the GIT. In one embodiment of this invention, the non-ionic vegetable oil GIT absorption enhancer of this invention is capable of opening tight junctions in the GIT, thereby increasing the transport of a drug from the GIT of an animal into the systemic system via the paracellular pathway. In another embodiment of this invention, the non-ionic vegetable oil GIT absorption enhancer of this invention is capable of increasing the transport of a drug via the transcellular pathway.

Preferred non-ionic vegetable oil GIT absorption enhancers according to this invention are natural vegetable oils or derivatives of the oils, especially ethoxylated natural vegetable oils in which a polyglycol chain has been inserted into the triglyceride molecule. Most preferred enhancers according to this invention are babassu oil, almond oil, maize oil, palm kernel oil, their ethoxylated derivatives or combinations thereof, especially the babassu oil, such as the Crovol oils obtained from Croda Oleochemicals.

Preferred drugs include drugs that, absent the non-ionic vegetable oil GIT absorption enhancer of this invention, are poorly absorbed via enteral, especially oral, routes including hydrophilic drugs or macromolecular drugs such as peptides, proteins or hormones. Heparin and heparinoids including low molecular weight heparin and thyrotropin releasing hormone are especially preferred drugs.

The invention also provides a method of enhancing the bioavailability of a drug following enteral, preferably oral, administration of the drug comprising enterally administering a pharmaceutically non-toxic, enhancing amount of a non-ionic vegetable oil GIT absorption enhancer to an animal either simultaneously with or prior to the administration of the drug.

The composition according to this invention can be administered enterally in a conventional solid or liquid pharmaceutical forms, e.g., tablets, film tablets, capsules, powders, granules, coated tablets or solutions. These can be prepared in a conventional manner and to do so the drug can be mixed with conventional pharmaceutical auxiliaries, such as tablet binders, fillers, preservatives, tablet disintegrators, flow regulators, plasticizers, wetting agents, dispersants, emulsifiers, solvents and/or retarding agents.

DETAILED DESCRIPTION OF THE INVENTION

As used in this specification and appended claims, the singular forms "a", "an" and "the" include plural referents unless the content clearly dictates otherwise. Thus, for example, reference to "a vegetable oil" includes a mixture of two or more vegetable oils, reference to a "a drug" includes reference to one or more drugs, and the like.

As used herein, the term "non-ionic vegetable oil GIT absorption enhancer" refers to a natural vegetable oil or a derivative of the oil, particularly an ethoxylated vegetable oil in which a polyglycol chain has been inserted into the triglyceride molecule, which is capable of enhancing the transport of a drug, particularly a hydrophilic and/or macromolecular drug such as a peptide, across the GIT in an animal such as a human. Such absorption enhancers include but are not limited to babassu oil, almond oil, maize oil, palm kernel oil, castor oil, coconut oil, cotton seed oil, jojoba oil, linseed oil, mustard oil, olive oil, peanut oil, safflower oil sesame oil, soybean oil, sunflower-seed oil and wheat germ oil, their ethoxylated derivatives or combinations thereof. Preferred oils are babassu oil, almond oil, maize oil and palm kernel oil, most preferably babassu oil, such as the Crovol oils obtained from Croda Oleochemicals, England.

As used herein, the term "drug" includes any drug appropriate for administration via the enteral, especially oral, route including conventional drugs. The term "drug" also explicitly includes those entities that are poorly absorbed via enteral, especially oral, routes including hydrophilic drugs or macromolecular drugs such as peptides, proteins or hormones including, but not limited to, insulin, calcitonin, calcitonin gene regulating protein, atrial natriuretic protein, colony stimulating factor, betaseron, erythropoietin (EPO), interferons such as α, β or γ interferon, somatropin, somatotropin, somatostatin, insulin-like growth factor (somatomedins), luteinizing hormone releasing hormone (LHRH), tissue plasminogen activator (TPA), thyrotropin releasing hormone (TRH), growth hormone releasing hormone (GHRH), oxytocin, estradiol, growth hormones, leuprolide acetate, factor VIII, interleukins such as interleukin-2, and analogues thereof and anti-coagulant agents such as heparin, heparinoids, hirudin, and analogues thereof. The term "drug" also includes nano- or microparticulate drug delivery systems in which a drug is entrapped, encapsulated by, associated with, or attached to a nano- or microparticle.

As used herein, a "therapeutically effective amount" of a non-ionic vegetable oil GIT absorption enhancer refers to an amount of enhancer that allows for uptake of therapeutically effective amounts of the drug via enteral administration.

EXAMPLE 1

Solubility, osmolarity and pH of various oils. The following oils were obtained from Croda Oleochemicals, England: Babassu oil (Crovol BA70G), Almond oil (Crovol A40; Crovol A70), Maize oil (Crovol M40; Crovol M70) and Palm kernel oil (Crovol PK40; Crovol PK70). These oils, which are stable and nonionic in nature, consist of several vegetable types, some having two levels of ethoxylation. A polyglycol chain has been inserted into the triglyceride molecule to impart water dispersibility or solubility. The solubility of the various oils was assessed in Hanks+Hepes at 37° C. as shown in Table 1.

TABLE 1

| Concentration | Almond Oil A40 | Palm Kernel PK40 | Maize Oil M40 | Almond Oil A70 | Palm Kernel PK70 | Maize Oil M70 | Babassu Oil BA70G |
|---|---|---|---|---|---|---|---|
| 0.1 mM | soluble | insoluble | insoluble | soluble | soluble | soluble | soluble |
| 5 mM | insoluble | insoluble | insoluble | soluble | soluble | soluble | soluble |
| 10 mM | insoluble | insoluble | insoluble | soluble | soluble | soluble | soluble |
| 40 mM | | | | | | | soluble |

The solublility of the various oils in a 75:25 water to ethanol solution as assessed as shown in Table 2.

TABLE 2

| Concentration | Almond Oil A40 | Palm Kermel PK40 | Maize Oil M40 |
|---|---|---|---|
| 20 mM | insoluble | insoluble | insoluble |

The osmolarity and pH of a range of concentrations of Babassu oil in Hank's buffer was examined (0.8 mM–40 mM). The osmolarities were in the range of 277–302 mOsm/L (acceptable osmolarity values for a physiological buffer should be in the range of 280–320 mOsm/L) and the pH values ranged from pH 7.23 to 7.3. 2 mM Almond oil (A70), 2 mM Maize oil (M70) and 2 mM Palm Kernel oil (PK70) has osmolarity values of 319, 319 and 322 mOsm/L, respectively, while their respective pH values were pH 7.33, 7.37 and 7.39.

EXAMPLE 2

Flux of Kraeber LMW Heparin across Caco-2 monolayers treated with Babassu oil (BA70G). The availability of intestinal cell lines which can be grown as monolayers on permeable filters to an epithelium-structure has made it possible to study properties and responses of epithelial cells without interference of the lamina propria. The Caco-2 cell line is derived from a lung metastasis of a human colon adenocarcinoma in a 72-year old male (ATCC designation: CCL 248). When cultured on polycarbonate filters, Caco-2 cells form a confluent monolayer with several properties characteristic of differentiated intestinal epithelial cells. The cell layers are morphologically distinct and have well defined brush borders at their apical surface. They exhibit characteristic active transport systems and display low permeability to non-specific transepithelial passage of macromoleucles. Additionally, the reproducibility and long term viability of the in vitro model, together with the ability to conveniently perform qualitative and quantitative transport studies across an intact epithelial layer, confer significant advantages over other in vitro models used for absorption studies. As such, transport studies of entities such as drugs or absorption enhancers across Caco-2 monolayers are predictive of transport of these entities across gastrointestinal tract cell layers in an animal such as a human.

Caco-2 cells were cultured in Dulbecco's Modified Eagles Medium (DMEM) 4.5 g/l glucose supplemented with 1% (v/v) non-essential amino acids, 10% foetal calf serum (FCS) and 1% penicillin/streptomycin. The cells were cultured at 37° C. and 5% $CO_2$ in 95% relative humidity. The cells were grown and expanded in normal tissue culture flasks and were passaged once they attained 100% confluence. The Caco-2 cells were then seeded on polycarbonate filters (Costar, 12 mm diameter, 0.4 μm pore size) at a density of $5 \times 10^5$ cells/cm$^2$ and incubated in six-well culture plates with a medium change every second day for the first six days and subsequently everyday. Confluent monolayers between day 20 and day 30 post seeding on filters were routinely used for the transepithelial transport studies.

Part a: Caco-2 monolayers (passage 20–40; 20–30 days post seeding on filters) were treated apically for 20–30 min with the 8mM and 40 mM Babassu oil in Hanks+25 mM Hepes. The oil was removed and replaced with Hanks containing 100 IU/ml Kraeber low molecular weight heparin. Samples were taken from the apical side at T=0 and T=120 min and from the basolateral side at T=60 min and T=120 min and tested in the Factor Xa assay as shown in Table 3. Transepithelial electrical resistance (TEER) measurements were taken at regular intervals for 20 min and subsequently every 30 min after the oil was removed with the Evohmeter (WPI) and chopsticks as shown in Table 4. The results are expressed as mean±S.E. (statistical differences examined using the two sided independent t-test). The TEER values of treated monolayers were only significantly different after 20 min, P<0.0001.

TABLE 3

Percentage Kraeber low molecular weight heparin transported to the basolateral side of Caco-2 monolayers after treatment with Babassu oil

| Time (min) | 8 mM Babassu oil, 100 IU/ml Kraeber heparin (N = 3) | 40 mM Babassu oil, 100 IU/ml Kraeber heparin (N = 3) |
|---|---|---|
| 0–60 | 0.230* | 0.600 ± 0.160 |
| 0–120 | 0.463 ± 0.061 | 1.510 ± 0.310 |

*heparin found in the basolateral sample from 1 monolayer only

TABLE 4

Percentage resistance remaining of TEER at time = 0 over 2 hour flux

| Time (min) | Control 100 IU/ml Kraeber heparin (N = 2) | 8 mM Babassu oil, 100 IU/ml Kraeber heparin (N = 3) | 40 mM Babassu oil, 100 IU/ml Kraeber heparin (N = 3) |
|---|---|---|---|
| 0 | 100.0 ± 00.0 | 100.0 ± 00.00 | 100.0 ± 00.00 |
| 1 | 100.0 ± 00.0 | 100.0 ± 00.00 | 100.0 ± 00.00 |
| 3 | 99.5 ± 00.71 | 99.8 ± 00.29 | 99.3 ± 1.30 |
| 5 | 100.0 ± 00.00 | 80.8 ± 17.60 | 99.0 ± 1.80 |
| 10 | 99.0 ± 1.41 | 80.8 ± 6.70 | 86.8 ± 13.30 |
| 20 | 92.9 ± 10.00 | 47.7 ± 11.60 | 46.7 ± 6.20 |
| 30 | 84.5 ± 21.90 | 45.7 ± 8.00 | 35.8 ± 5.50 |
| 60 | 75.5 ± 17.70 | 49.7 ± 9.23 | 37.7 ± 12.10 |
| 90 | 74.3 ± 36.30 | 47.0 ± 5.68 | 39.0 ± 14.40 |
| 120 | 65.9 ± 34.20 | 39.7 ± 9.78 | 36.1 ± 7.12 |

Part b: 100 IU/ml Kraeber LMW heparin was added apically to Caco-2 monolayers in the presence of 0.8 mM, 4 mM, 8 mM and 40 mM Babassu oil at 37° C. in an incubator. Samples were taken from the apical sides at T=0 and 2 hours. Samples were taken from the basolateral sides at 30 min intervals over the 2 hour period as shown in Table 5 (0.8 mM babassu oil had no effect on the flux of heparin). TEER measurements were taken at T=3 min and T=10 min and subsequently every 30 min as Table 6.

TABLE 5

Percentage Kraeber low molecular weight heparin transported to the basolateral side of Caco-2 monolayers in the presence of Babassu oil

| Time (min) | 4 mM Babassu oil, 100 IU/ml Kraeber heparin (N = 6) | 8 mM Babassu oil, 100 IU/ml Kraeber heparin (N = 10) | 40 mM Babassu oil, 100 IU/ml Kraeber heparin (N = 3) |
|---|---|---|---|
| 0–60 | 0.000 ± 0.000 | 0.300 ± 0.004* | 0.373 ± 0.002 |
| 60–120 | 0.678 ± 0.050 | 1.344 ± 0.090 | 2.219 ± 0.160 |

*heparin found in the basolateral samples from 6 out of 10 monolayers

TABLE 6

Percentage resistance remaining of TEER at time = 0 over 2 hour flux

| Time (min) | Control 100 IU/ml Kraeber heparin (N = 4) | 4 mM Babassu oil, 100 IU/ml Kraeber heparin (N = 6) | 8 mM Babassu oil, 100 IU/ml Kraeber heparin (N = 10) | 40 mM Babassu oil, 100 IU/ml Kraeber heparin (N = 3) |
|---|---|---|---|---|
| 0 | 100.0 ± 00.0 | 100.0 ± 00.00 | 100.0 ± 00.00 | 100.0 ± 00.00 |
| 3 | 99.5 ± 0.00 | 100.0 ± 0.00 | 94.6 ± 3.53 | 86.5 ± 7.73 |

TABLE 6-continued

Percentage resistance remaining of TEER at time = 0 over 2 hour flux

| Time (min) | Control 100 IU/ml Kraeber heparin (N = 4) | 4 mM Babassu oil, 100 IU/ml Kraeber heparin (N = 6) | 8 mM Babassu oil, 100 IU/ml Kraeber heparin (N = 10) | 40 mM Babassu oil, 100 IU/ml Kraeber heparin (N = 3) |
|---|---|---|---|---|
| 10 | 99.0 ± 1.40 | 100.0 ± 0.00 | 100.0 ± 0.00 | 91.5 ± 9.33 |
| 30 | 95.8 ± 6.00 | 98.6 ± 1.96 | 51.9 ± 11.66 | 43.5 ± 9.15 |
| 60 | 92.9 ± 10.0 | 78.1 ± 7.19 | 36.8 ± 10.18 | 31.5 ± 12.87 |
| 90 | 73.6 ± 21.0 | 53.4 ± 1.69 | 34.6 ± 8.20 | 27.0 ± 11.75 |
| 120 | 69.7 ± 26.0 | 39.7 ± 2.70 | 30.9 ± 9.9 | 18.8 ± 10.08 |

Transmission electron microscopy, TEM, was carried out on the monolayers which had been treated with 0.8 mM, 4 mM, 8 mM and 40 m Babassu oil for 2 hours. No effect was seen on the integrity of the monolayers at 0.8 mM or 4 mM Babassu oil. At 8 mM oil, a low percentage of the junctions were slightly dilated but there was no cellular damage. Although the resistance measurements had decreased significantly in the monolayers treated with 40 mM oil, it was not until the TEM was carried out that is was apparent how toxic this concentration was to the cells. During preparation for TEM, most of the cells had come off the filters and those remaining suffered degradation.

The above clearly shows that 8 mM Babassu oil enhances the flux of heparin across Caco-2 monolayers without having an adverse effect on the monolayers. There were no differences seen regarding the effect of the Babassu oil on cell integrity or enhancement of flux using the oil as a pretreatment or as a component throughout the two hour flux. Babassu oil causes a drop in TEER; however, after the oil is removed and replaced with Hanks, the TEER remained at 50% and it did not recover. When present throughout the 2 hour flux, it causes TEER to drop initially followed by a gradual fall. From these results, one could assume that the enhancement route for heparin is probably predominantly transcellular as flux appears unrelated to the TEER and also because heparin is more likely to go across cells because of its physico-chemical properties.

EXAMPLE 3

Flux of Kraeber LMW Heparin across rat colon tissue treated with Babassu oil (BA70G). Rats of approximately 350 g in weight were dissected and samples of colon tissue were removed and washed in 1×Hank's Balanced Salt Buffer (HBSS; Gibco BRL, Cat # 14065-031). The tubular segment was cut along the mesenteric border to give a flat square piece of tissue. The smooth muscle layer was then removed by blunt dissection to leave an approximate 2.5 cm² patch of epithelium. The isolated rat colonic mucosae were mounted in Side-by-side Sweetana-Grass (SG) diffusion chambers in Hanks+NaHCO$_3$. After the tissue had equilibrated, 100 IU/ml Kraeber LMW heparin (8456 MW) was added to the apical side of the tissue in the presence of 8 mM Babassu oil. Samples were taken from the apical side at T=0 and 120 min. Samples were taken from the basolateral sides at 30 min intervals (results shown in Table 7). TEER measurements were taken every 30 min and the samples were tested in the Factor Xa assay (results shown in Table 8).

TABLE 7

Percentage Kraeber low molecular weight heparin transported to the basolateral side of rat colon tissue in the presence of Babassu oil

| Time (min) | 8 mM Babassu oil, 100 IU/ml Kraeber heparin (N = 4) |
|---|---|
| 0–60 | 0.000 ± 0.000 |
| 60–120 | 0.195 ± 0.077 |

TABLE 8

Percentage resistance remaining of TEER at time = 0 over 2 hour flux

| Time (min) | Control (100 IU/ml Kraeber heparin (N3)) | 8 mM Babassu oil, 100 IU/ml Kraeber heparin (N = 6) |
|---|---|---|
| 0 | 100 ± 00.0 | 100 ± 00.00 |
| 30 | 96 ± 3.46 | 91.5 ± 10.25 |
| 60 | 74 ± 17.9 | 85.65 ± 10.15 |
| 90 | 69 ± 8.57 | 88.0 ± 16.97 |
| 120 | 64 ± 15.8 | 83.5 ± 11.24 |

As given in Example 2 above, an increase in the flux of Kraeber LMW heparin across Caco-2 monolayers was detectable at 90 min whereas there seemed to be a longer lag period with rat colon in that heparin was only detectable on the basolateral side at 2 hours. Babassu oil did not have the same effect on the TEER measurements of the rat colon tissue as it did on the Caco-2 monolayers. When the flux of Kraeber heparin across Caco-2 monolayers was examined without the use of Babassu oil, no heparin was detectable in the basolateral samples.

EXAMPLE 4

Figure 1:
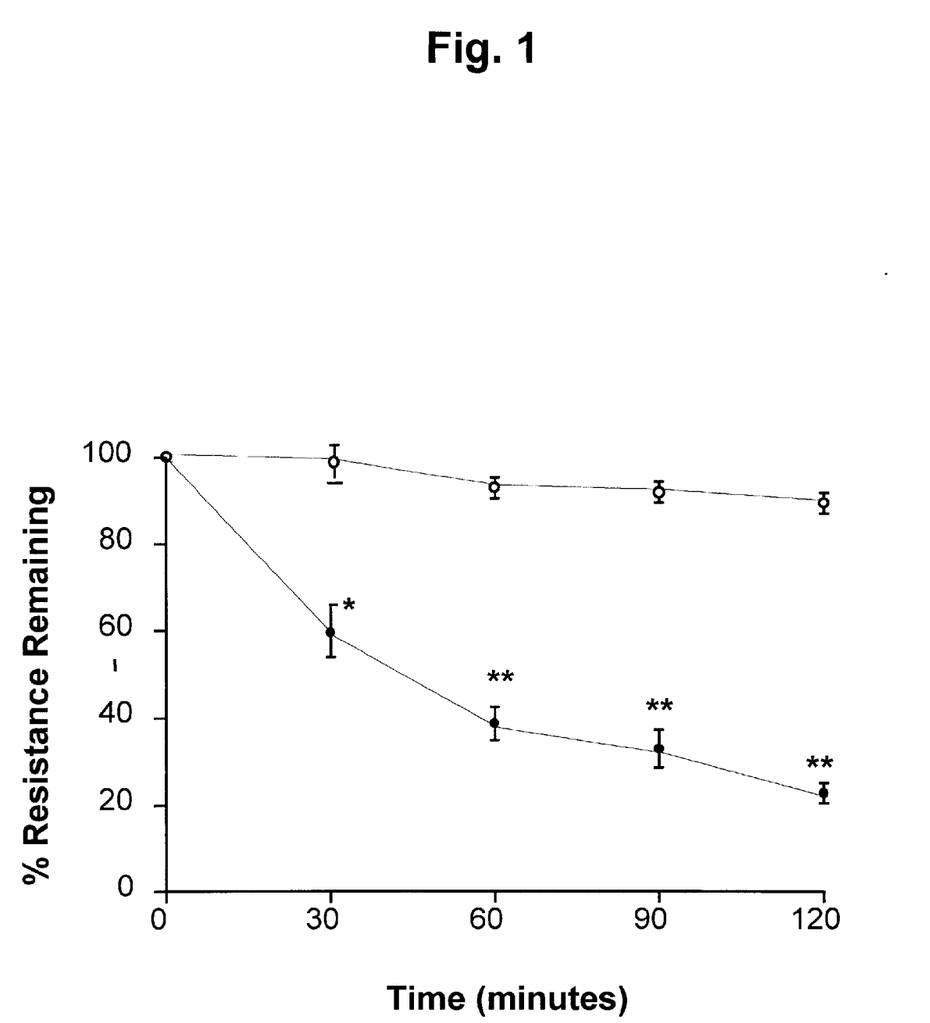
FIG. 1 shows the effect of 8 mM Babassu oil added apically at time zero on TEER of Caco-2 monolayers (cells: day 21, P30–31) over a two hour period (transport study of [$^3$H]-mannitol). [$^3$H]-mannitol TEER (open circles; N=9); [$^3$H]-mannitol and 8 mM Babassu oil (closed circles; N=5) (*P=<0.05 and **P=<0.005 (obtained using 2-tailed unpaired student t-test))

Flux of mannitol across Caco-2 monolayers treated with Babassu oil (BA 70G) or Cytochalasin D. The effect of Babassu oil on the flux of mannitol (mannitol, D -[1-$^3$H (n)]; specific activity: 15–30 Ci/mmol; NEN DuPont) across Caco-2 monolayers was examined by applying 1 μCi/ml (a concentration of 0.04 nM) mannitol in the presence of 1% Babassu oil (8 mM) to Caco-2 monolayers prepared as given in Example 2 for 2 hours. The cell monolayers were incubated with prewarmed Hanks balanced salt solution (HBSS modified by adding 1 g glucose/l—final concentration 11 mM glucose and 24 mM Hepes, pH 7.4) at 37° C. for 30 minutes, adding 1 ml to apical and 2 ml to the basolateral side. At T=0, apical HBSS was replaced with 1 ml HBSS containing the mannitol transport solution and the plates were placed in a 37° C. incubator on an orbital shaker. Samples were taken from the apical side at T=0 and T=120 min and from the basolateral side every 30 min. The resulting samples were measured by liquid scintillation spectrophotometry using a Wallac 1409. The apparent permeability coefficient ($P_{app}$, cm/sec) values were found to increase from $0.79\times10^{-6}$ for the control (N=6; mannitol flux across Caco-2) to $2.19\times10^{-6}$ for mannitol flux across Caco-2 monolayers in the presence of 1% Babassu oil (N=5) (P=0.001). TEER measurements (Millicell ERS) were taken throughout the 2 hour flux at 30 min intervals as shown in FIG. 1. These results demonstrate that mannitol was without effect on TEER with respect to loss of TEER in the controls (not treated with Babassu oil). However, a statistically significant decrease in TEER was induced by treatment with 8 mM Babassu oil. In the first 60 minutes there was a dramatic reduction of 60% which then became more gradual during the remaining 60 minutes.

Mannitol has been shown to be restricted to transport via extracellular routes and has proved to be of considerable use in the quantification of paracellular pathway modification in intestinal model cell lines. The above results confirm that Babassu oil also has a definite effect on the paracellular pathway as there is a 3-fold increase in the flux of mannitol in monolayers treated with the oil as opposed to no treatment with the oil.

Figure 2:
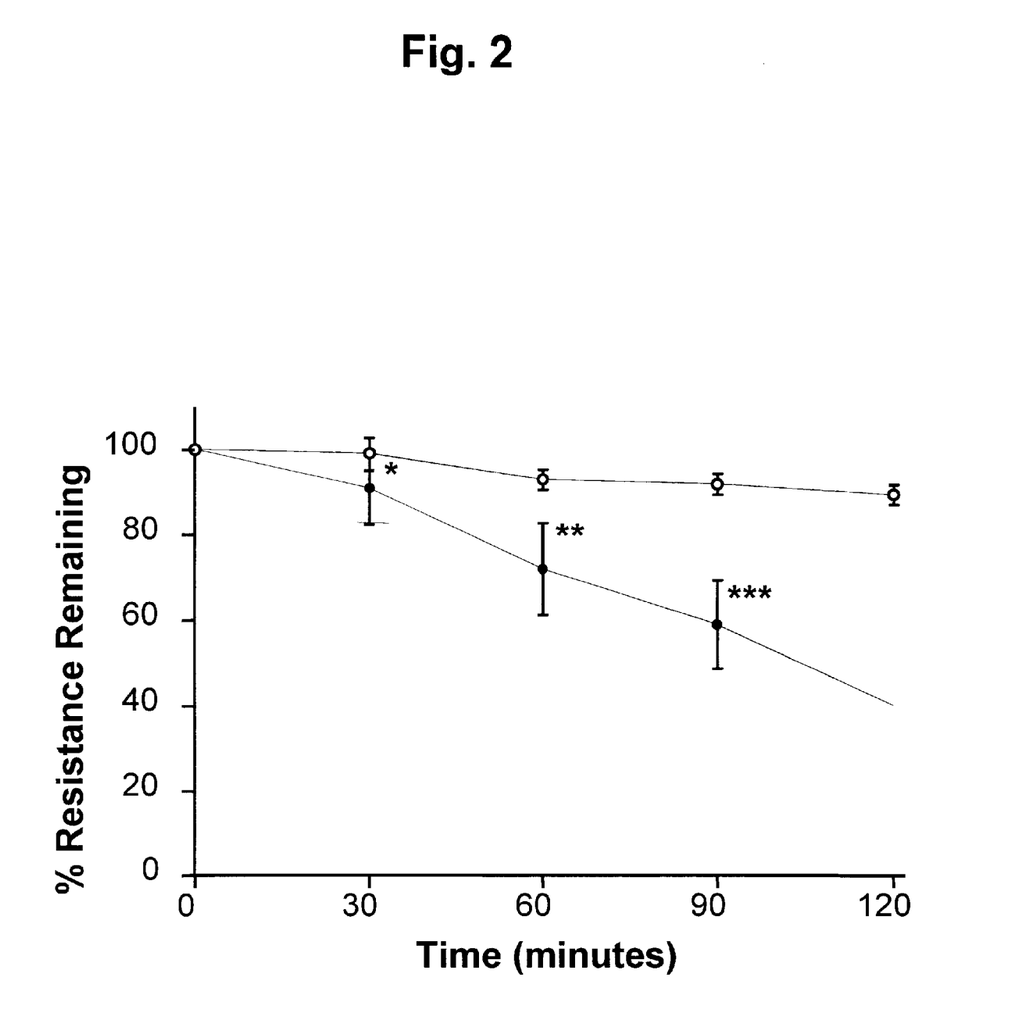
FIG. 2 shows the effect of 1 $\mu$g/ml Cytochalasin D added apically and basolaterally at time zero on TEER of Caco-2 monolayers (control cells: day 21, P31; cells & Cytochalasin D: day 27, P34) over a two hour period (transport study of [$^3$H]-mannitol). [$^3$H]-mannitol TEER (open circles; N=9); [$^3$H]-mannitol and 1 $\mu$g/ml Cytochalasin D (closed circles; N=6) (*P=0.04, P=0.004 and *P=0.001 (obtained using 2-tailed unpaired student t-test))

An experiment similar to the above transepithelial transport of mannitol experiment was conducted except that cytochalasin D (1 µg/ml), a potent tight junction opener, was added apically and basolaterally at time zero instead of the Babassu oil. As above, TEER measurements were taken as shown in FIG. 2. Similar to the Babassu oil experiment, these results demonstrate that mannitol was without effect on TEER with respect to loss of TEER in untreated preparations (not treated with cytochalasin D). A reduction in TEER of 60% was observed in the presence of the tight junction opener cytochalasin D. However, the observed decrease in TEER in the presence of cytochalasin D was not as significant as that observed when Babassu oil was added apically at T=0. The apparent permeability coefficient ($P_{app}$, cm/sec) for mannitol increased to $3.15\times10^{-6}$ (P<0.0001)in the presence of cytochalasin D. These results show that a similar enhancement of mannitol flux occurs in the presence of 8 mM babassu oil as was observed in the presence of Cytochalasin D, indicating a possible mechanism of action for babassu oil similar to the tight junction opener, cytochalasin D.

EXAMPLE 5

Recovery of Caco-2 monolayers after exposure to Babassu oil (BA70G). The ability of Caco-2 monolayers to recover after exposure to Babassu oil was investigated by treating monolayers with 8 mM Babassu oil for an incubation period of 2 hours at 37° C. in Hanks+Hepes (similar to Examples 2 and 4 above). After this incubation period, the monolayers were rinsed gently in complete culture medium and were replaced in the $CO_2$ incubator at 37° C. TEER measurements were taken at 1, 2, 20 and 24 hours in culture. Untreated monolayers were set up in Hanks as a control measure (N=3). The resistance measurements of all the treated monolayers returned to those obtained originally in culture medium and actually increased with respect to the control monolayers. Thus, although there was up to a 50% reduction in TEER across the monolayers after treatment with 8 mM Babassu oil, this effect was transient and the monolayers were able to recover.

EXAMPLE 6

Flux of [$^3$H]-TRH across Caco-2 monolayers treated with Babassu oil (BA 70G) or Cytochalasin D. Thyrotropin releasing hormone (TRH) is the hypothalamic peptide that regulates the synthesis and secretion of thyroxine T4 and triiodothyronine from the thyroid gland. TRH absorption occurs principally in the upper small intestine with little or no absorption occurring in the middle or lower small intestine. TRH is thought to be absorbed predominantly passively through a paracellular route between the cells.

TRH is given currently by intravenous injection in the diagnosis of disorders of the hypothalmic-pituitary-thyroid axis for mild hyperthyroidism, hypothyroidism and opthalmic Graves' disease. It is also under investigation in the prevention of neonatal respiratory distress syndrome.

The effect of Babassu oil on the flux of TRH (specific activity: 70–90 Ci/mmol; NEN DuPont) across Caco-2 monolayers was examined by applying 0.12 nM TRH in the presence of 1% Babassu oil (8 mM) to Caco-2 monolayers prepared as given in Example 2 for 2 hours. The cell monolayers were incubated as given in Example 4 above. At T=0, apical HBSS was replaced with 1 ml HBSS containing the TRH transport solution and the plates were placed in a 37° C. incubator on an orbital shaker. Samples were taken from the apical side at T=0 and T=120 min and from the basolateral side every 30 min. The resulting samples were measured by liquid scintillation spectrophotometry using a Wallac 1409.

Figure 3:
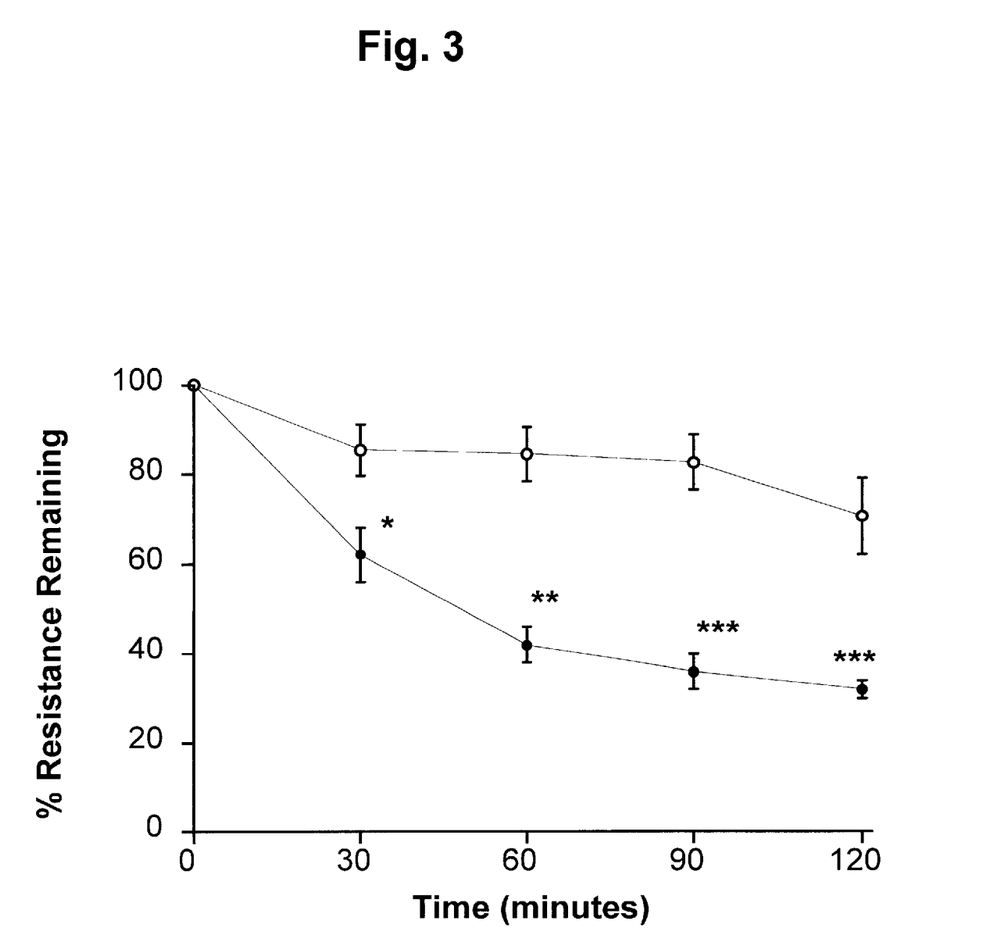
FIG. 3 shows the effect of 8 mM Babassu oil added apically at time zero on TEER of Caco-2 monolayers (control cells: day 27, P31, cell & 8 mM Babassu oil: day 27, P34) over a two hour period (transport study of [$^3$H]-TRH). [$^3$H]-TRH TEER (open circles; N=4); ); [$^3$H]-TRH and 8 mM Babassu oil (closed circles; N=5) (*P=0.002, **P= 0.009 and P=0.0001 (obtained using 2-tailed unpaired student t-test))

The apparent permeability coefficient ($P_{app}$, cm/sec) values were found to increase from $0.53\times10^{-6}$ for the control (N=4; TRH flux across Caco-2) to $2.87\times10^{-6}$ for TRH flux across Caco-2 monolayers in the presence of 1% Babassu oil (N=5). TEER measurements (Millicell ERS) were taken throughout the 2 hour flux at 30 min intervals as shown in FIG. 3. These results demonstrate that TRH was without effect on TEER with respect to loss of TEER in the controls (not treated with Babassu oil). However, a statistically significant decrease of 78.2% in TEER was induced by treatment with 8 mM Babassu oil during the flux.

Figure 4:
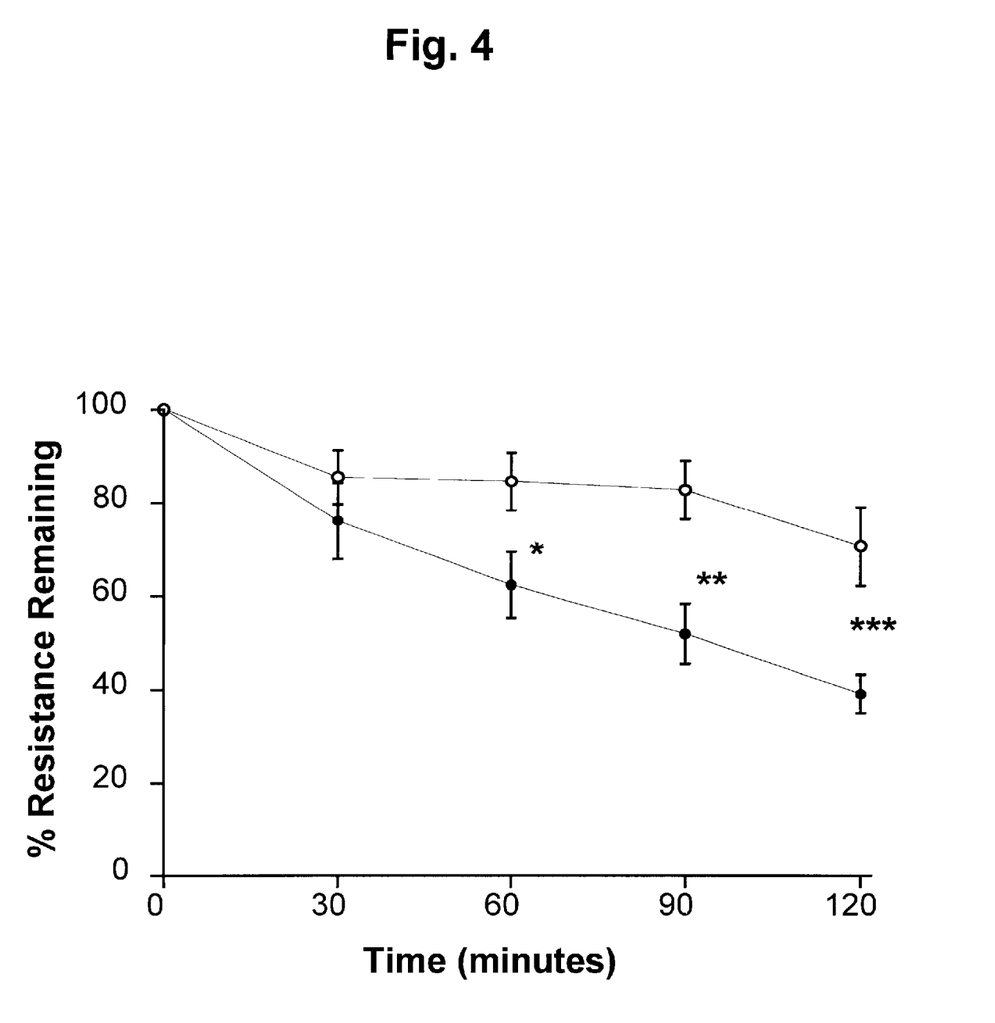
FIG. 4 shows the effect of 1 $\mu$g/ml Cytochalasin D added apically and basolaterally at time zero on TEER of Caco-2 monolayers (control cells: day 27, P31; cells & Cytochalasin D: day 25, P42) over a two hour period (transport study of [$^3$H]-TRH). [$^3$H]-TRH TEER (open circles; N=4); [$^3$H]-TRH and 1 $\mu$g/ml Cytochalasin D (closed circles; N=6) ((*P=0.04, P=0.0083 and *P=0.005 (obtained using 2-tailed unpaired student t-test))

An experiment similar to the above transepithelial transport of TRH experiment was conducted except that cytochalasin D (1 µg/ml), a potent tight junction opener, was added apically and basolaterally at time zero instead of the Babassu oil. As above, TEER measurements were taken as shown in FIG. 4. Similar to the Babassu oil experiment, these results demonstrate that TRH was without effect on TEER with respect to loss of TEER in untreated preparations (not treated with cytochalasin D). Similar to the mannitol results given in Example 4 above, there was an initial reduction of 40% in TEER during the first hour of the flux with an additional 22% reduction in the remaining hour in the presence of cytochalasin D. The observed decrease in TEER in the presence of cytochalasin D was not as significant as that observed when Babassu oil was added apically at T=0. The apparent permeability coefficient ($P_{app}$, cm/sec) for TRH increased to $5.7\times10^{-6}$ cm/sec in the presence of cytochalasin D. These results show that a similar enhancement of TRH flux occurs in the presence of 8 mM babassu oil as was observed in the presence of Cytochalasin D.

Figure 5:
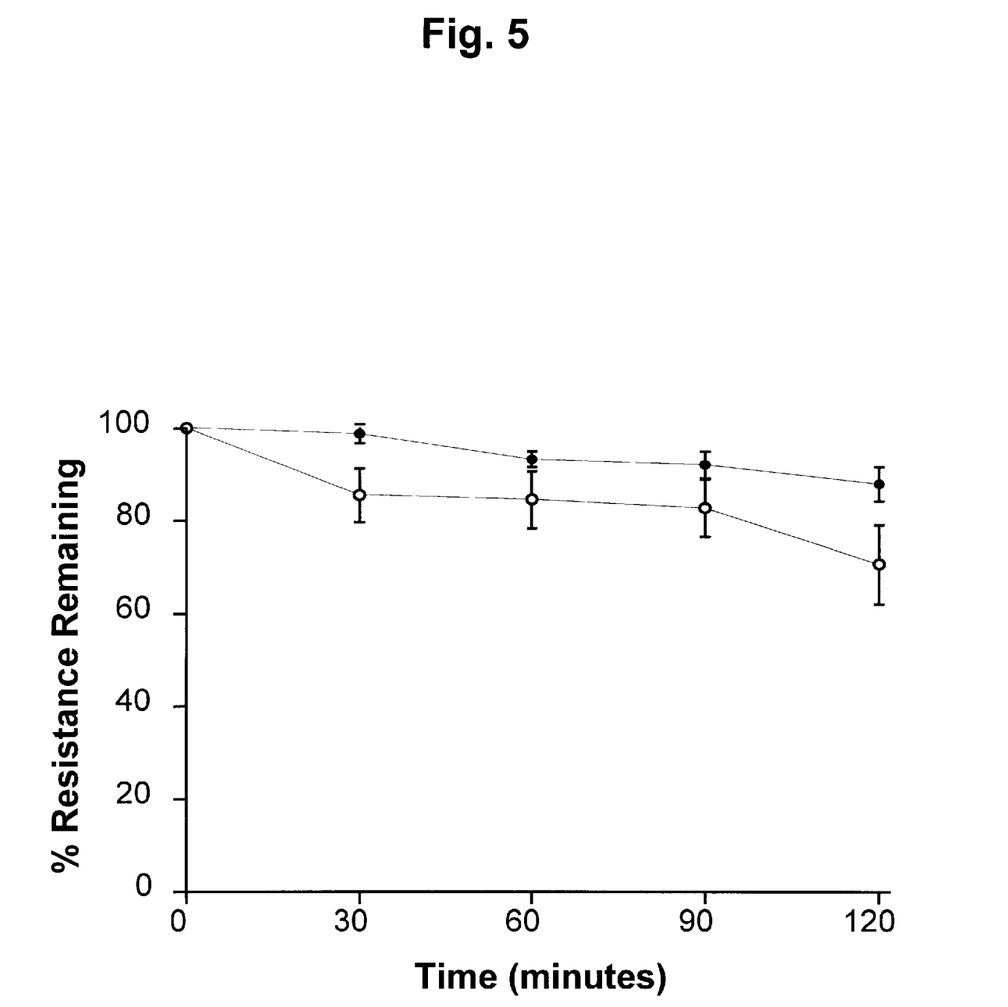
FIG. 5 shows the effect of excess cold TRH added apically at time zero on TEER of Caco-2 monolayers (control cells: day 27, P31; cells & excess cold TRH: day 25, P42) over a two hour period (transport study of [$^3$H]-TRH). [$^3$H]-TRH TEER (open circles; N=4); [$^3$H]-TRH and excess cold TRH (closed circles; N=6)

A further 2 hour transepithelial transport study was carried out as above for [$^3$H]-TRH (0.12 nM) except that excess TRH (cold, 4.4 mM; Bachem, UK) was also administered apically. FIG. 5 shows that there is a similar reduction in TEER of approximately 20% in the presence and absence of an excess of cold TRH. Statistical analysis carried out at each time point did not yield any significant difference between TEER reduction of TRH control cells and that of cells exposed to an excess of cold TRH. A [$^3$H]-TRH $P_{app}$ of $0.69 \times 10^{-6}$ cm/sec was observed in the presence of excess cold TRH. No significant difference between TRH $P_{app}$ values at low concentrations (0.05–0.1 nM) and high TRH concentrations (4.4 mM) was observed providing evidence of passive TRH absorption across the monolayer.

Both [$^3$H]-mannitol and [$^3$H]-TRH control TEER values did not decrease significantly during the 2 hour flux experiments of Examples 4 and 6 with an overall decrease of 12.8% in resistance of mannitol control cells and a decrease of 29.2% in TRH control cells. Upon addition 1% (8 mM) babassu oil added apically at time zero, a statistically significant decrease in the TEER of the Caco-2 monolayers was recorded. Those cells exposed to the [$^3$H]-mannitol solution containing 8 mM babassu oil [$^3$H]-exhibited a decrease of 79.4% in TEER. Similarly, those exposed to [$^3$H]-TRH solution containing 8 mM babassu oil exhibited a reduction of 77.1%.

The results of these studies demonstrate that the flux of TRH, like mannitol, was linear and did not differ significantly from that of mannitol. The similarity between mannitol and TRH transport across the Caco-2 monolayers and the similarity of the enhancement of the flux of both drugs across the monolayers in the presence of Babassu oil evidences a possible paracellular mechanism of transport for TRH across Caco-2 monolayers.

The results of the cytochalasin D flux experiments provide further evidence for paracellular transport of TRH. Cells exposed to both [$^3$H]-mannitol and cytochalsin D (added apically and basolaterally at time zero) and those exposed to [$^3$H]-TRH and Cytochalasin D (added apically and basolaterally at time zero) exhibited a decrease in TEER of 59% and 50% respectively during the 2 hour flux experiments. As predicted, the tight junction opener, Cytochalasin D caused a statistically significant enhancement of the flux of both [$^3$H]-mannitol and [$^3$H]-TRH across the monolayers and similarly increased the $P_{app}$ of both [$^3$H]-mannitol and [$^3$H]-TRH in the presence of the tight junction opener. These results indicate that Babassu oil enhances TRH absorption in a similar manner to Cytochalasin D, i.e., the Babassu oil mediated enhancement of TRH absorption was as a result of tight junction opening.

The results of flux experiments with [$^3$H]-TRH in the presence of excess cold TRH added apically at time zero, yielded a $P_{app}$ for TRH which was not significantly different from that obtained for [$^3$H]-TRH at low concentrations. This result indicates that TRH absorption is concentration independent, is passive, and occurs through a paracellular route between the cells.

TRH is typically given in doses of 200–500 µg (100 µg/ml) to reach a therapeutic plasma concentration of 0.04 mg/L. The surface area of the filter used in this study was 1.13 Cm$^2$ and the absorbing surface area of the small intestine is ~125 m$^2$. By correlating these two figures, an estimate of the TRH concentration required to achieve therapeutic plasma concentration when administered orally can be made. It was observed that 0.2% TRH was transported across the Caco-2 monolayer in 1 hours. Babassu oil provided an enhancement of the flux to 1% transported in 1 hour. For instance, rather than having to use 5 mg/L solutions of TRH to achieve the peroral therapeutic concentrations, only 0.4 mg/L solutions are required if they are administered with an enhancing amount of Babassu oil.

EXAMPLE 7

Flux of heparin across Caco-2 monolayers treated with Maize oil (M70) or Palm Kernel oil (PK70). Following the procedures of the 2 hour flux experiments of Example 2, Part b, unfractionated heparin (600 IU/ml) was added apically to Caco-2 monolayers in the presence of 0.1 mM, 1.0 mM, 2.0 mM and 3 mM Maize oil and 0.1 mM and 4 mM Palm Kernel oil. TEER measurements were taken every 30 minutes and the 10 µl aliquots of the apical and basolateral samples were frozen at −20° C. until ready to analyse. Heparin transport across the monolayers was measured using the FXA heparin assay. No transport of heparin across the monolayers was observed in the presence of Maize or Palm Kernel Oil at these concentrations.

EXAMPLE 8

Flux of [$^3$H]-mannitol or [$^3$H]-TRH across Caco-2 monolayers treated with Maize oil (M70), Palm Kernel oil (PK70), Almond oil (A 70) or Babassu oil (BA70G). Following the procedures of the 2 hour flux experiments of Example 4 above, [$^3$H]-mannitol (0.04 nM) was added apically to Caco-2 monolayers in the presence of 0.1 mM, 5.0 mM, and 10 mM Almond Oil, 0.1 mM, 2.0 mM, 2.5 mM, 5.0 mM and 10 mM Palm Kernel oil as well as 0.1 mM, 1 mM and 2 mM Maize oil. TEER measurements were taken every 30 minutes for each experiment. For Almond oil and Palm Kernel oil at 5 and 10 mM, approximately a 70% reduction in TEER was observed which was constant during the course of the two hour flux. Based on the marked reduction in TEER and evident toxicity at 5 and 10 mM, a lower concentration of 2 mM was chosen. Flux of 2 mM Maize oil resulted in a linear decrease in TEER of approximately 10% at each 30 minute interval.

Figure 6:
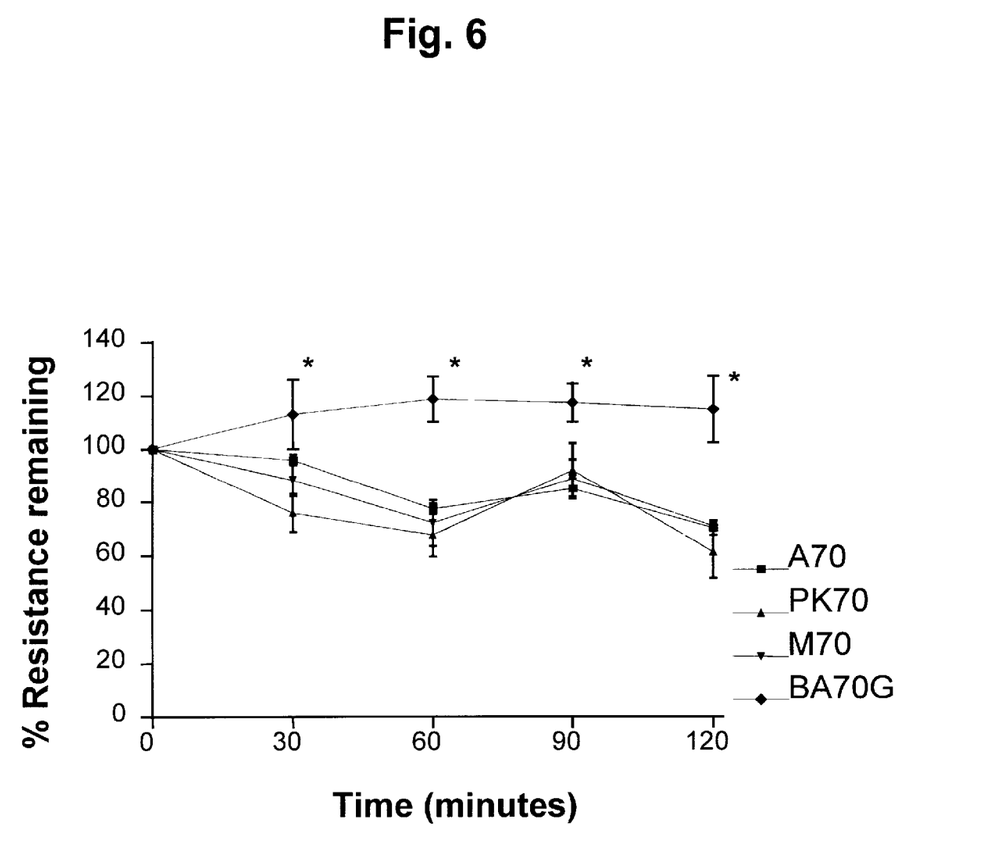
FIG. 6 shows the effect of 2 mM Almond oil (A70; —■—), 2 mM Palm Kernel oil (PK70; —▲—), 2 mM Maize oil (M70; —▼—) and 2 mM Babassu oil (BA70G; —♦—) added apically at time zero on TEER of Caco-2 monolayers over a two hour period (transport study of [$^3$H]-TRH) expressed as % resistance remaining (*statistically significant difference between Babassu oil TEER results and the remaining oils at each 30 minute interval except at t=30 min there was no significant difference in TEER between Babassu oil and Almond oil)

FIG. 6 shows the effect of apical administration of [$^3$H]-TRH (0.2 nM) in the presence of Almond oil, Palm Kernel oil, Maize oil and Babassu oil (each oil at a concentration of 2 mM) following the flux procedures given in Example 6 above. Statistically significant differences existed between Babassu TEER results and those of the other oils (2 mM) at each 30 minute interval except between Babassu oil and Almond oil at the T=30 sampling. No significant differences in TEER was observed between Almond oil, Palm Kernel oil and Maize oil. The average 30% reduction in TEER observed for Almond, Palm Kernel and Maize oils at 2 mM during the 2 hour flux was not evident in the presence of Babassu oil (2 mM).

Apical-to-basolateral fluxes of the hydrophilic marker molecule $^3$H-mannitol and $^3$H-TRH in the presence of each of the four oils at a concentration of 2mM demonstrated a 2 to 3 fold increase in transport across Caco-2 monolayers. A summary of these transepithelial transport results is given in Table 9.

TABLE 9

Summary of Transepithelial Transport Results for Various Oils

| Drug/Enhancer | No. of exp. | $P_{app}$ cm/sec × $10^{-6}$ ± SEM | % Transport per hour | Fold increase in Transport |
|---|---|---|---|---|
| [$^3$H]-mannitol control (0.04 nM) | 4 | 0.79 ± 0.03 | 0.28 | |
| Mannitol & Almond Oil | | | | |
| [$^3$H]-mannitol & Almond Oil (0.1 mM) | 3 | 1.970 ± 0.07 | 0.68 | 2.45 |
| [$^3$H]-mannitol & Almond Oil (5.0 mM) | 3 | 1.91 ± 0.02 | 0.69 | 2.46 |
| [$^3$H]-mannitol & Almond Oil (10 mM) | 3 | 7.413 ± 0.41 | 2.67 | 9.56 |
| Mannitol & Palm Kernel Oil | | | | |
| [$^3$H]-mannitol & Palm Kernel (0.1 mM) | 3 | 2.83 ± 0.52 | 1.02 | 3.64 |
| [$^3$H]-mannitol & Palm Kernel (2.0 mM) | 4 | 2.28 ± 0.136 | 0.82 | 2.9 |
| [$^3$H]-mannitol & Palm Kernel (2.5 mM) | 4 | 2.49 ± 0.143 | 0.89 | 3.17 |
| [$^3$H]-mannitol & Palm Kernel (5.0 mM) | 3 | 5.87 ± 0.54 | 2.11 | 7.56 |
| [$^3$H]-mannitol & Palm Kernel (10 mM) | 3 | 13.63 ± 2.42 | 4.92 | 17.55 |
| Mannitol & Maize Oil | | | | |
| [$^3$H]-mannitol & Maize Oil (0.1 mM) | 2 | 3.39 ± 0.25 | 1.22 | 4.35 |
| [$^3$H]-mannitol & Maize Oil (1.0 mM) | 2 | 3.625 ± 0.19 | 1.31 | 4.67 |
| [$^3$H]-mannitol & Maize Oil (2.0 mM) | 2 | 6.175 ± 2.73 | 2.23 | 7.96 |
| [$^3$H]-TRH control (0.2 nM) | 2 | 0.72 ± 0.025 | 0.26 | |
| [$^3$H]-TRH & Almond Oil (2.0 mM) | 4 | 1.45 ± 0.08 | 0.52 | 2 |
| [$^3$H]-TRH & Maize Oil (2.0 mM) | 3 | 2.203 ± 0.48 | 0.79 | 3.03 |
| [$^3$H]-TRH & Palm Kernel Oil (20 mM) | 4 | 1.146 ± 0.09 | 0.412 | 1.58 |
| [$^3$H]-TRH & Babassu Oil (2.0 mM) | 4 | 1.189 ± 0.08 | 0.43 | 1.65 |

Recovery of Caco-2 monolayers after exposure to Palm Kernel Oil (PK70), Almond Oil (A 70), Maize Oil (M70) and Babassu oil (BA 70G). The ability of Caco-2 monolayers to recover after exposure to various oils at differing concentrations was investigated by treating monolayers with an oil for an incubation period of 2 hours at 37° C. in Hanks+Hepes (similar to Examples 2, 4 and 8 above). The TEER of the Caco-2 monolayers was first recorded in culture and the monolayers were incubated in prewarmed Hanks for 30 minutes after which the resistance was recorded. The apical Hanks was removed and replaced with 1 ml of a particular oil at a particular concentration. Resistance measurements were recorded at 30 minute intervals throughout the two hour incubation period. After this incubation period, the monolayers were rinsed gently in prewarmed complete culture medium and were replaced in the $CO_2$ incubator at 37° C. TEER measurements were taken at 1, 20 and 24 hours in culture. Untreated monolayers were set up in Hanks as a control measure (N=3). Following two hour flux experiments with the various oils at concentrations ranging from 0.1 to 10 mM, Caco-2 monolayers once replaced in culture conditions recovered with 24 hours (except for Maize oil at 2 mM). Table 10 summarizes the results of these recovery experiments.

EXAMPLE 10

Toxicity Tests for Palm Kernel Oil (PK70), Almond Oil (A 70), Maize Oil (M70) and Babassu oil (BA 70G). Two tests were employed to identify the toxic potential of the various oils used in the preceding examples. The Neutral Red Toxicity Test assesses cell viability based on lysosomal integrity. The neutral red dye is incorporated into the intact lysosomes of living cells whereas dead cells no longer possess the uptake system necessary to carry out this process. The amount of spectrophotometrically-measured dye uptake is indicative of the numbers of viable cells.

TABLE 10

Results of Recovery Experiments

| Time, Hours | 0.1 mM | 2 mM | 5 mM | 10 mM |
|---|---|---|---|---|
| | | % Resistance Remaining | | |
| Control | | | | |
| 1 | 78.3 | | | |
| 2 | 88.9 | | | |
| 21 | >100 | | | |
| | N =3 | N = 4 | N = 3 | N = 3 |
| Palm Kernel Oil (PK70) | | | | |
| 1 | 72.3 | 18.0 | 13.0 | 5 |
| 20 | 105.8 | 95.0 | 129.9 | 172 |
| 24 | 92.0 | 101.0 | 98.5 | 123 |
| Almond Oil (A70) | | | | |
| 1 | 62.7 | | 70.9 | 16 |
| 20 | 88.2 | | 144.8 | 232 |
| 24 | 88.8 | | 136.5 | 184 |
| Maize Oil (M70) | | | | |
| 1 | 84.6 | 20 | 28.65 | 16.65 |
| 20 | | 76 | | |
| 24 | 95.2 | 52 | 117.9 | 102.2 |
| Babassu Oil (BA70G) | | | | |
| 1 | | 59 | | |
| 4 | | 66 | | |

TABLE 10-continued

Results of Recovery Experiments

| Time, Hours | 0.1 mM | 2 mM | 5 mM | 10 mM |
|---|---|---|---|---|
| 20 | | 67 | | |
| 24 | | 92 | | |

For the Neutral Red Toxicity Test, confluent cells are harvested (e.g., using 2 ml trypsin for approximately 4 min at 37° C.) and counted using standard operating procedures such as the trypan blue dye exclusion test. A 100 µl cell suspension containing $10^5$ cells was added to each well of a 96 well plate; 3 wells containing 100 µl medium only was used as a blank. The cells were incubated for 24 hours at 37° C. Appropriate dilutions such as 1:6 dilution of 0.6, 30, 60 mM Almond oil and Palm kernel oil was carried out to yield final concentrations (e.g., 0.1, 5 and 10 mM) and 20 µl of each concentration was added to the 100 µl cell suspension in each well. Following incubation of the cells for two culture medium was removed and the cells were washed with 100 µl warm PBS. 100 µl of neutral red solution was added to each well and incubated at 37° C. for 4 hours at which point the medium was removed and the cells were rinsed with neutral red fixative. Following removal of the fixative, 100 µl of neutral red solubilization solution was added to each well for 10 minutes and the absorbance was read on a spectrophotometer at 570 nm. Table 11 provides the results of the Neutral Red Toxicity Test for various concentrations of Almond oil, Palm Kernel oil and Babassu oil.

TABLE 11

Results of Neutral Red Toxicity Test

| | % of Control | | |
|---|---|---|---|
| Conc. (mM) | Almond Oil (A70) | Palm Kernel Oil (PK70) | Babassu Oil (BA70G) |
| 0.1 | 98.3 | 94.06 | |
| 0.8 | | | 100 |
| 5 | 21.32 | 20.05 | |
| 8 | | | 100 |
| 10 | 21.77 | 32.76 | |
| 40 | | | 9 |

The MTT Assay measures mitochondrial dehydrogenase (MDH) activity as a marker of cell viability. MDH is only present in viable cells and can convert the yellow tetrazolium salt MMT to a purple crystalline formazan product. The amount of this product is directly proportional to the number of viable cells.

Figure 7:
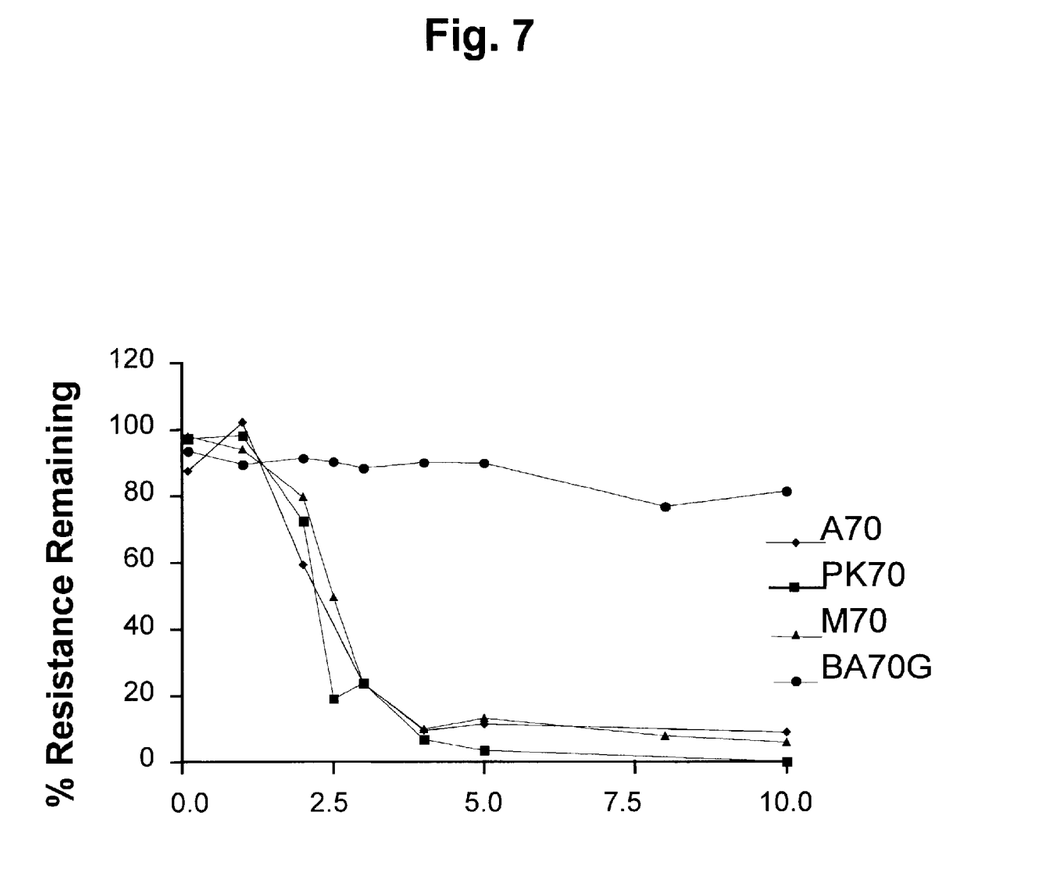
FIG. 7 shows a graph of % of control v. concentration (mM) curves for the MTT Assay for Almond oil (A70: —♦—), Palm Kernel oil (PK70: —■—), Maize oil (M70: —▲—), and Babassu oil (BA70G: —●—).

For the MTT Assay, cells were harvested and counted using standard procedures. 100 µl of cell suspension was added to 48 wells and the cells were incubated at 37° C. for 24 hours. Appropriate dilutions are made of the various oils and 20 µl of each concentration was added to the 100 µl suspension in each well. Following a two hours incubation period, 10 µl of the MTT labelling reagent is added to each well for 4 hours. 100 µl solubilization solution is added to each well, the plate is incubated for 24 hours and the absorbance of each well is measured using a spectrophotometer at 570 nm. Table 12 and FIG. 7 provide a summary of the MTT Assay results for various concentrations of Almond Kernel oil, Maize oil and Babassu oil. The results of the MTT toxicity test indicate that between 2 and 3 mM there is a significant increase in the toxic potential of Almond oil, Maize oil and Palm Kernel oil. However, at concentrations ranging from up to 10 mM, it appears that Babassu oil is considerably less toxic and is minimally toxic (9%) at 10 mM. Thus, for Almond oil, Maize oil and Palm Kernel oil, a narrow concentration range around 2–3 mM is necessary to avoid marked toxicity while still maintaining a 2–3 fold increase in transport across Caco-2 monolayers demonstrated by all four oils. Babassu oil, however, is much less toxic at a concentration five fold higher than the toxicity limit for the other oils. This finding is important because the limits in the use of any penetration enhancer may be dictated by their potential toxicities.

TABLE 12

Results of MTT Assay

| | % of Control | | | |
|---|---|---|---|---|
| Conc. (mM) | Almond oil (A70) | Palm Kernel oil (PK70) | Maize oil (M70) | Babassu oil (BA70G) |
| 0.1 | 87.39 | 97.33 | 97.96 | 93.62 |
| 1 | 102.26 | 98.19 | 93.98 | 89.48 |
| 2 | 59.34 | 72.5 | 79.71 | 91.4 |
| 2.5 | | 19.07 | 49.62 | 90.29 |
| 3 | 23.67 | 23.8 | 23.55 | 88.3 |
| 4 | 9.45 | 6.74 | 9.85 | 90 |
| 5 | 11.4 | 3.52 | 13.13 | 89.8 |
| 8 | | | 7.8 | 76.84 |
| 10 | 8.84 | 0.0472 | 4.83 | 81.39 |

Structural analysis was also used to measure the toxicity of the oils. TEMs were taken of Caco-2 monolayers subsequent to 2 hour exposure to palm Kernel oil (PK70) and Maize oil (M70), both at a concentration of 2 mM. The integrity of the monolayers was intact. However, dispersion of the microvilli and some junction opening was apparent.

The ability of the Babassu, Almond, Maize and Palm Kernel oils to enhance the flux of the paracellular marker mannitol and TRH implies that this enhancement may be mediated by opening tight junctions. 0.7% per hour transport of Kraeber LMW heparin across Caco-2 monolayers was demonstrated in the presence of Babassu oil (8 mM). The most likely path for heparin, due to its molecular weight of 20 Kd, is transcellular. Therefore the mechanism of action for the non-ionic vegetable oil GIT absorption enhancers of this invention is unclear although they appear to be able to enhance the permeation of agents across or between cells in the gastrointestinal tract according to the physicochemical properties of the particular drug and with minimal toxic effects and transient effects on the cell layers in the gastrointestinal tract.

What is claimed is:

1. A pharmaceutical composition for enhancing the absorption of a drug from the gastrointestinal tract of an animal comprising an enteral form comprising a therapeutically effective amount of a non-ionic vegetable oil gastrointestinal is tract (GIT) absorption enhancer, wherein the absorption enhancer is babassu oil or a derivative thereof, and wherein the absorption enhancer does not form a lipid vesicle.

2. The composition of claim 1, wherein the drug is a macromolecular drug.

3. A pharmaceutical composition of claim 1 wherein the drug is selected from the group consisting of peptides and proteins.

4. A pharmaceutical composition of claim 1 wherein the drug is heparin or a heparinoid.

5. A pharmaceutical composition of claim 1 wherein the drug is a hormone selected from the group consisting of thyrotropin releasing hormone, calcitonin, somatropin, lutenizing hormone releasing hormone, growth hormone releasing hormone, oxytocin, estradiol, leuprolide acetate and growth hormones.

6. The composition of claim 1, wherein the composition is an oral composition.

7. A method for enhancing the absorption of a drug from the gastrointestinal tract of an animal without significant toxic side effects comprising the step of enterally administering an enteral form comprising a therapeutically effective amount of a non-ionic vegetable oil GIT absorption enhancer prior to enterally administering an enteral form comprising a drug, wherein the absorption enhancer does not form a lipid vesicle and wherein the non-ionic vegetable oil GIT absorption enhancer and the drug can be in the same enteral form or separate enteral forms and wherein the absorption enhancer is a natural vegetable oil or derivative thereof selected from the group consisting of babassu oil, almond oil, maize oil, palm kernel oil, ethoxylated derivatives thereof and combinations thereof.

8. The method of claim 7, wherein the absorption enhancer is a natural vegetable oil or derivative thereof selected from the group consisting of babassu oil, almond oil, maize oil, palm kernel oil, ethoxylated derivatives thereof and combinations thereof.

9. A method for enhancing the absorption of a drug from the gastrointestinal tract of an animal without significant toxic side effects comprising the step of enterally administering an enteral form comprising a therapeutically effective amount of a non-ionic vegetable oil GIT absorption enhancer simultaneously with or prior to enterally administering an enteral form comprising a drug, wherein the absorption enhancer is babassu oil or a derivative thereof and wherein the absorption enhancer does not form a lipid vesicle and wherein the non-ionic vegetable oil GIT absorption enhancer and the drug can be in the same enteral form or separate enteral forms.

10. The method of claim 7, wherein the drug is selected from the group consisting of hydrophilic drugs and macromolecular drugs.

11. The method of claim 7, wherein the drug is selected from the group consisting of peptides, proteins and hormones.

12. A method for enhancing the absorption of a drug from the gastrointestinal tract of an animal without significant toxic side effects comprising the step of enterally administering an enteral form comprising a therapeutically effective amount of a non-ionic vegetable oil GIT absorption enhancer simultaneously with or prior to enterally administering an enteral form comprising a drug, wherein the drug is heparin or a heparinoid, and wherein the absorption enhancer does not form a lipid vesicle and wherein the non-ionic vegetable oil GIT absorption enhancer and the drug can be in the same enteral form or separate enteral forms, and wherein the absorption enhancer is a natural vegetable oil or derivative thereof selected from the group consisting of babassu oil, almond oil, maize oil, palm kernel oil, ethoxylated derivatives thereof and combinations thereof.

13. The method of claim 7, wherein the administration is oral.

14. The method of claim 7, wherein the absorption enhancer increases the absorption of the drug from the gastrointestinal tract via the paracellular pathway.

15. The method of claim 7, wherein the absorption enhancer increases the absorption of the drug from the gastrointestinal tract via the transcellular pathway.

\* \* \* \* \*